United States Patent

Sasaki et al.

[11] 4,238,428
[45] Dec. 9, 1980

[54] PROCESS FOR MAKING A PRILLED PRODUCT

[75] Inventors: Susumu Sasaki; Tamikazu Takemota; Shoji Tomita, all of Fujieda, Japan

[73] Assignee: Sumitomo Durez Company, Ltd., Tokyo, Japan

[21] Appl. No.: 960,549

[22] Filed: Nov. 14, 1978

[30] Foreign Application Priority Data

Nov. 25, 1977 [JP] Japan .................................. 52-140662

[51] Int. Cl.³ .............................................. B01J 2/04
[52] U.S. Cl. ........................................ 264/13; 264/39
[58] Field of Search ..................................... 264/13, 39

[56] References Cited

U.S. PATENT DOCUMENTS

| | | | |
|---|---|---|---|
| 2,898,625 | 8/1959 | Chao ......................................... | 425/6 |
| 3,642,393 | 2/1972 | Ross et al. ................................. | 425/6 |

Primary Examiner—Donald E. Czaja
Assistant Examiner—James R. Hall
Attorney, Agent, or Firm—Peter F. Casella; James F. Mudd

[57] ABSTRACT

In a process for making a prilled product from a molten substance therefor steam or heated gas is intermittently introduced into the prilling apparatus to clean the apparatus. In one embodiment the molten substance is passed through a filter zone prior to introduction to a nozzle provided with orifices to produce the prilled product and the flow of molten substance through the filter zone is periodically interrupted and steam or heated gas is passed through the filter zone in the direction opposite to the flow of molten substance to clean the filter zone. More than one filter zone can be operated in parallel so that while one filter zone is being cleaned, molten substance is passed through another filter zone to provide for continuous operation of the process.

3 Claims, 2 Drawing Figures

PROCESS FOR MAKING A PRILLED PRODUCT

BACKGROUND OF THE INVENTION

The present invention relates to an improvement in the process for making prills from a melted substance, and more particularly to a process for cleaning the system through which said melted substance passes.

Various processes have been proposed for making prills from highly hydroscopic substances such as urea or from substances which are difficult to handle in powder form, thereby improving the flowability and preventing dust generation. Among these, the principal approach is the melt prilling process, and particularly widely employed is the so-called spray prilling process in which a melted substance is made to flow down or sprayed from the top of a tower by a nozzle with small holes or by centrifugal force with a rotary disc, and prills are obtained either by drying or solidifying the dropping liquid particles through countercurrent gas introduced from the bottom of tower, or by dropping said liquid particles into a medium being inert to said melted substance.

In such prilling process, smooth passage of the melted substance through the nozzle is an important factor, and it is imperative for realizing a continuous operation. The key factors identified for enabling such continuous operation are (1) pre-heating the nozzle in order to prevent viscosity increase of melted substance in the vicinity of the nozzle at the start of the prilling process, (2) quick removal of impurities inevitably contained in the melted substance which give rise to clogging of the nozzle, and (3) applicability of a desirable treatment at the end of the prilling operation, to be explained hereinafter.

For example, during the prilling operation, the nozzle can be partially or totally clogged within a short period by impurities such as dust present in the melted substance or by scale resulting from scorched material. A total clogging of the nozzle will naturally disable the performance of the process, while partial clogging of the nozzle will result in formation of relatively large dripping liquid particles which drop in unsolidified state and stick to the bottom of the tower. The presence of such sticking unsolidified substance will cause reheating, by the heat accumulated therein, of other particles even if they have been completely solidified during the drop, thereby resoftening such particles and thus forming a deposit on the bottom of tower, rendering difficult the discharge of prilled product. It therefore becomes necessary to interrupt the operation and remove the deposit formed on the bottom of the tower. Such deposit, being a defective product, not only reduces the yield of production but also hinders continuous operation. In order to prevent such troubles, it is necessary to provide a strainer in the system between the melting tank and the nozzle for removing the impurities and scale.

On the other hand, upon termination of the operation, in case the melted substance remaining in the system is not removed and left standing, the pathway of melted substance in the prilling apparatus, including the pipes, strainer, pump, spray chamber, nozzle, valves and the like, become clogged by the solidified substance which renders re-start of operation impossible. Also even if the melted substance is removed partially, the remaining melted substance will become deteriorated by the heat of pre-heating to form scales in the system, thus resulting in clogging of the nozzle at the re-start of operation. Further, this step, when repeated, will result in accumulation of a substantial amount of scale in the system, which can only be removed by overhauling the entire system. This phenomenon, therefore, leads to the formation of defective product as explained in the foregoing and hinders continuous operation.

The object of the present invention is to provide a prilling process allowing continuous prill formation economically with a simple apparatus.

SUMMARY OF THE INVENTION

According to the present invention, the abovementioned object is achieved by passing a melted substance through a strainer containing a filter and periodically back flushing the filter with steam or heated gas to clean the filter, and by cleaning the prilling system such as pipes, strainers, spray chamber, nozzle, valves and the like, through which the melted substance passes, with steam or heated gas after the prilling operation.

DESCRIPTION OF PREFERRED EMBODIMENT

The melted substance referred to in the present invention includes concentrated solutions and melted slurries which solidify at ambient temperature or a lower temperature but liquidify at a higher temperature. Examples of such melted substances are wax, paraffin, polyolefins, fatty acids, organic acids, rosins, naphthalene, higher alcohols, phthalic anhydride, bisphenol-A, sulfur, urea, phenolic resins, epoxy resins, alkyd resins, petroleum resins, coumarone-indene resins, pitch, and the like.

The nozzle referred to in the present invention includes an ordinary pressurized nozzle, a two-fluid nozzle, a perforated plate nozzle providing a spray by gravity or by additional pressure, and a rotary disc nozzle.

The back-washing or back-flushing referred to in the present invention is meant to separate the impurities and scale caught in the filter in the strainer from said filter by blowing steam or heated gas from a direction opposite to the flow of melted substance and to remove such impurities and scale thus separated from the filter.

Figure 1:
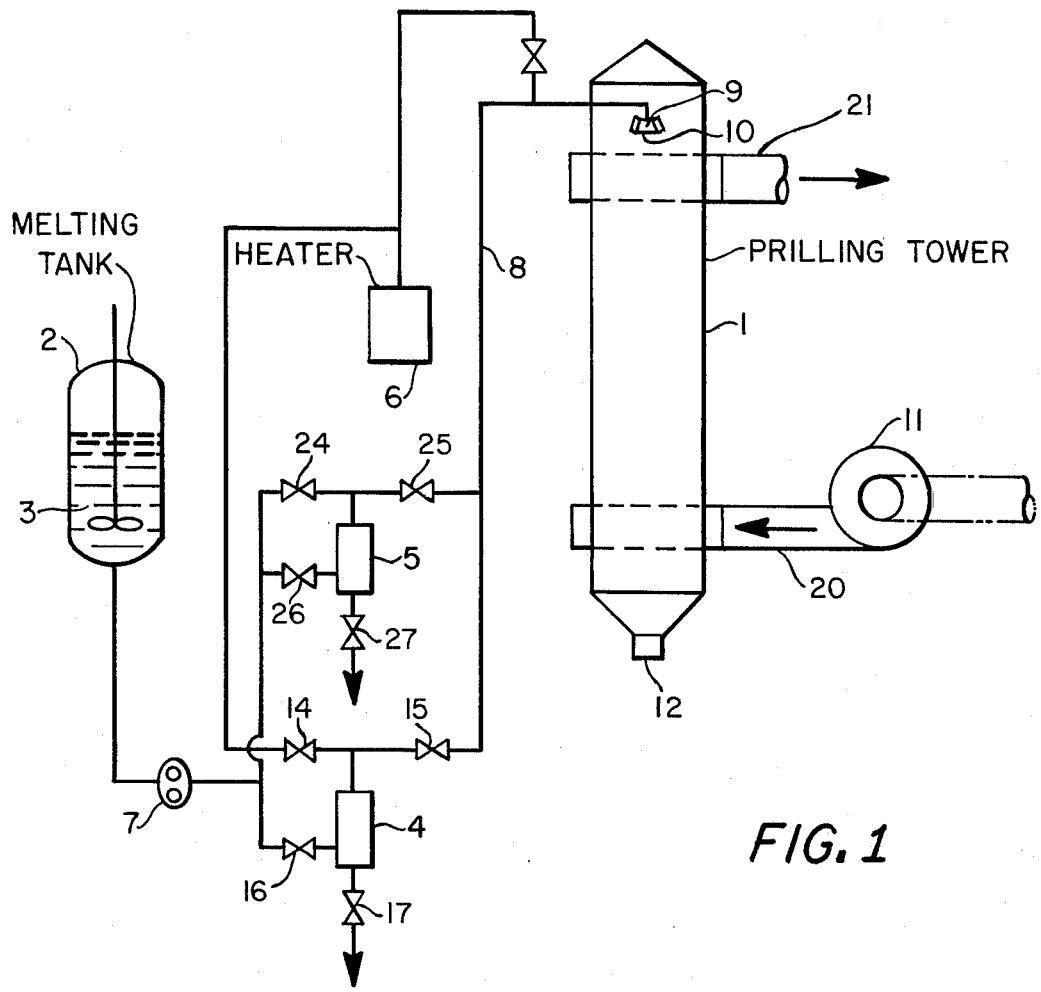
Figure 2:
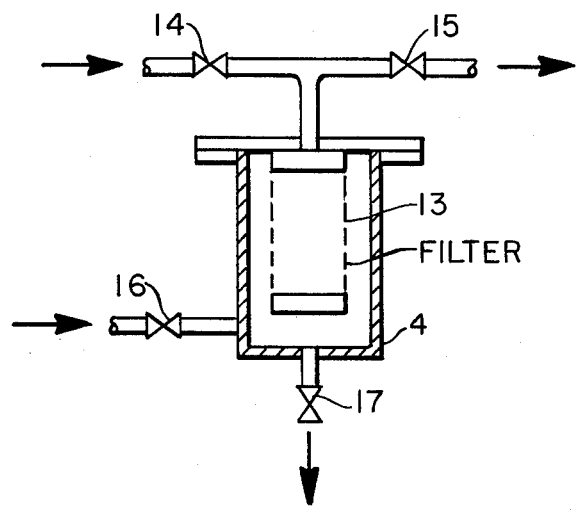

Now the prilling process of the present invention will be explained in the following description which makes reference to the accompanying drawings, in which FIG. 1 is a schematic explanatory view of the apparatus of the present invention, and FIG. 2 is a cross-sectional view of the strainer or filter zone.

FIG. 1 shows prilling tower 1, melting tank 2 for melting a substance, melted substance 3, strainer 4, strainer 5, steam or heated gas generating device 6, pump 7, piping 8 preferably of double-wall structure for heating, spray chamber 9 nozzle 10, fan 11, discharge outlet 12, air inlet conduit 20 and air outlet conduit 21, and valves 14, 15, 16, 17, 24, 25, 26 and 27.

FIG. 2 shows the details of strainer 4 and 5 which have a filter 13 (preferably 80 mesh), valve 14 for blowing steam or heated gas through the filter 13 and out of valve 17, valve 15 for supplying the nozzle 10 with the melted substance from which impurities and scales are removed in the strainer, valve 16 for supplying the melted substance from the melting tank to the strainer, and valve 17 for discharging impurities and scales at the back-washing.

According to the present invention, the aforementioned system is cleaned by blowing steam or heated gas thereinto.

The pressure of steam or temperature of heated gas is determined according to the species of the melted substance. In the case of steam, a pressure range of 2.5 to 11 kg/cm$^2$G is preferred, particularly from 5 to 8 kg/cm$^2$G, while in the case of heated gas a temperature range of 110° to 200° C. is preferred. The heated gas is provided with a pressure for example of 1 to 5 kg/cm$^2$G. The heated gas is preferably an inert gas so as not to adversely affect the melted substance. Air is also usable for this purpose.

The cleaning operation of the prilling system according to the present invention is divided into that during the prilling operation and that after the operation. The cleaning during the operation is achieved by closing the valves 15 and 16 in front of and behind the strainer 4 and opening the valves 17 and 14 whereby the steam or heated gas is blown into the strainer 4 to back-wash the filter (metal netting) thus separating impurities and scales there from and discharging these materials from drain valve 17 of the strainer by means of steam or heated gas. The strainer, shown as a vertical structure in FIG. 2, may also be of another structure. If the strainer is not cleaned, the filter (metal netting) will become clogged with impurities and scales present in the melted substance, substantially obstructing prill formation from the melted substance. The strainer is indispensable for removing impurities and scales and for obtaining satisfactory prill products since, in the absence of the strainer, the nozzle at the top of tower becomes clogged and inhibits continuous operation. If there is only one strainer, the prilling operation will temporarily be interrupted during the back-washing of the strainer. Although such temporary interruption is not a particular problem for the operation, production inevitable becomes intermittent. It is therefore preferable to provide 2 to 8 strainers, and to alternately conduct back-washing thereof. For example operation is first performed with the first strainer 4, and when back-washing is required, continuous operation is achieved merely by switching the valve to the second strainer 5. The strainer 4 is back-washed with steam or heated gas during the use of said strainer 5. By repeating such operation alternately it is possible to remove the impurities and scales caught in the strainer readily from the system, and thus to achieve a continuous operation, avoiding nozzle-clogging.

It is not possible in said back-wash, to completely eliminate the impurities and scales from the filter (metal netting) by merely employing water or pressurized gas of ambient temperature or by applying a negative pressure.

The cleaning of the system at the end of operation is conducted by blowing steam or heated gas into the entire system immediately after termination of operation. The entire system can be cleaned easily and completely for example by opening drain valve 17 at the bottom of the strainer and blowing steam or heated gas from the top of the tower.

The cleaning after termination of the operation cannot be satisfactorily conducted with water or a pressurized gas of ambient temperature. Cleaning with a solvent may be considered, but the use of solvents in a system for elevated temperature involves danger.

As explained in the foregoing description, continuous operation which has been the most important target in the prill preparation is for the first time achieved by the process and apparatus of the present invention, which, allowing economical production of prills of good quality, is extremely valuable for industrial application.

In the following the present invention will be further clarified by a non-limitative example in which rference is made to the apparatus of FIGS. 1 and 2.

EXAMPLE

A petroleum resin (Escorez 1102B; Esso) was melted and heated to 230° C. in melting tank 2, in which the free space was filled with nitrogen gas in order to prevent deterioration of said resin. The petroleum resin thus melted contained a very small amount of dust and scales. Successively the nozzle was preheated, and the prilling operation was started utilizing the entire system including the strainer, pipes, spray chamber and the like. The valves were operated in such a manner that the flow passes through the strainer 4, having a filter composed of a metal netting of 80 mesh. The nozzle employed was a plate nozzle provided with 25 small holes or orifices. The strainer 4 became clogged 3 hours after the start of operation, which was identified by an increase in pump pressure and a decrease in prill operation rate. The pump pressure and production rate returned to normal when the value was switched so as to use strainer 5. The strainer 4, which dismantled in this state, showed almost complete clogging on one surface of the metal netting with impurities and scales. At this stage the strainer 4 was back-washed by opening the drain valve and blowing steam of 7 kg/cm$^2$ G for 20 minutes from the top, whereby melted petroleum resin rich in impurities and scales was discharged. The strainer, when dismantled in this state, showed almost no adhesion of impurities and scales on the metal netting. As clogging was again observed 3 hours later, the operation was again switched back to strainer 4, while strainer 5 was backwashed with steam of 7 kg/cm$^2$ G for 20 minutes in the same manner as mentioned in the case of strainer 4. The prilling operation was continued for 32 hours by repeating the above-mentioned operation. Upon termination of the operation, all the heating for pipings, strainers, spray chamber etc. was terminated, and steam for 7 kg/cm$^2$ G was blown into the pipe close to the spray chamber at the top of tower for 50 minutes while maintaining the drain valve of each strainer open. By this operation the melted petroleum resin present in the spray chamber was completely discharged through the nozzle while that in the piping was completely discharged from the drain valve of the strainers. In this manner prill production was successfully conducted continuously for one month by repeating the above-mentioned operation.

The present invention can be used in connection with the inventions disclosed in applications entitled "Prilling Process", Ser. No. 960,694, "Nozzle Pre-Heating Device in Prilling Apparatus", Ser. No. 960,693, and "Process for Making Prills From Melted Substance and Apparatus Therefor", Ser. No. 960,692, all filed on even date herewith, the disclosures of which are incorporated herein by referene.

We claim:
1. In a process for making a prilled product comprising:
 (a) passing a molten substance through one or more orifices in a nozzle disposed in the upper portion of the prilling zone, and
 (b) solidifying the resulting droplets of molten substance as said droplets fall through said prilling zone, the improvement comprising:
- (c) passing said molten substance through a filter zone prior to introduction of the molten substance to said orifice,
- (d) interrupting the flow of a molten substance through said orifice and filter zone, and
- (e) introducing steam or heated gas through the orifice, filter zone and prilling zone to clean the nozzle, filter zone and prilling zone.

2. In a process for making a prilled product comprising:
- (a) passing a molten substance through an orifice disposed in the upper portion of the prilling zone, and
- (b) solidifying the resulting droplets of molten substance as said droplets fall through said prilling zone, the improvement comprising:
- (c) passing said molten substance through a first filter zone prior to introduction to said orifice,
- (d) periodically interrupting the flow of molten substance through said filter zone, and
- (e) passing steam or heated gas through the filter zone in the direction oppsite to the flow of molten substance to clean the filter zone.

3. The process of claim 2 wherein the molten substance is passed through a second filter zone during the time in which steam or heated gas is passed through the first filter zone, and thereafter interrupting the flow of molten substance to the said second filter zone and passing steam or heated gas or a combination thereof through the second filter zone in the direction opposite to the flow of molten substance.

* * * * *